(12) United States Patent
Lambrou

(10) Patent No.: US 12,702,295 B2
(45) Date of Patent: Aug. 11, 2026

(54) METHODS AND APPARATUS FOR SCREENING FOR MALADIES BY RETINAL SCAN

(71) Applicant: Fred H Lambrou, Jacksonville, FL (US)

(72) Inventor: Fred H Lambrou, Jacksonville, FL (US)

( * ) Notice: Subject to any disclaimer, the term of this patent is extended or adjusted under 35 U.S.C. 154(b) by 669 days.

(21) Appl. No.: 17/495,295

(22) Filed: Oct. 6, 2021

(65) Prior Publication Data

US 2022/0104703 A1 Apr. 7, 2022

Related U.S. Application Data

(60) Provisional application No. 63/088,134, filed on Oct. 6, 2020.

(51) Int. Cl.

| | |
|---|---|
| *A61B 3/12* | (2006.01) |
| *A61B 3/00* | (2006.01) |
| *A61B 3/10* | (2006.01) |
| *A61B 3/117* | (2006.01) |
| *A61B 3/135* | (2006.01) |
| *A61B 5/00* | (2006.01) |

(52) U.S. Cl.

CPC .............. *A61B 3/12* (2013.01); *A61B 3/0058* (2013.01); *A61B 3/102* (2013.01); *A61B 3/1176* (2013.01); *A61B 3/135* (2013.01); *A61B 5/0013* (2013.01); *A61B 5/4088* (2013.01); *A61B 5/7275* (2013.01)

(58) Field of Classification Search

CPC ..... A61B 3/0025; A61B 3/0058; A61B 3/102; A61B 3/1176; A61B 3/12; A61B 3/135; A61B 5/0013; A61B 5/4088; A61B 5/7275; G06T 7/0012; G06T 2207/30041

See application file for complete search history.

(56) References Cited

U.S. PATENT DOCUMENTS

2021/0275021 A9 9/2021 Katz et al.

OTHER PUBLICATIONS www.Globecheck.com, “Welcome to Globechek. What we see may save your sight.”, accessed Oct. 6, 2021.

*Primary Examiner* — Jack Dinh

(74) *Attorney, Agent, or Firm* — Rogers Towers, P.A.; Trace H. Jackson

(57) ABSTRACT

The present disclosure provides for an ophthalmic testing system that may prescreen for ophthalmic diseases and systemic diseases. In some embodiments, an OTS may provide general screening results and relatives scores to patients that may be at risk for diabetic retinopathy, macular degeneration, or Alzheimer’s. In some implementations, the OTS may offer self-screening features without collecting personal information that may identify the individual. In some embodiments, the OTS may use artificial intelligence and machine learning and machine learning to provide accurate and instant analysis and results to a user.

17 Claims, 16 Drawing Sheets

METHODS AND APPARATUS FOR SCREENING FOR MALADIES BY RETINAL SCAN

BACKGROUND

The eyes are the window to the soul and to the brain. A person's retina is an outcropping of their brain. A retinal scan provides the easiest, least-invasive method of checking on the health of the brain Doctors recommend eye exams at least once a year to test for poor vision or diseases causing blindness. Many people avoid eye doctors due to cost or lack of insurance. Others complain of the difficulty to make an appointment within a reasonable amount of time. Scheduling an appointment may require a patient to take the day off work, move their schedule around, and may have difficulty finding an appointment time that works with their schedule. This is compacted when insurance coverage is also a part of that calculation. In some parts of the world, eye doctors are simply unavailable to large swaths of the population. In short, many eye-related maladies go undiagnosed because of missed routine eye exams.

Many eye diseases, including those resulting in complete blindness, may be completely prevented or cured with early detection. Macular degeneration leads to decreased vision or, in severe cases, permanent vision loss. Macular degeneration may be treated if caught early. Glaucoma is another common eye disease that generally leads to blindness except when caught and treated early. Moreover, nuclear cataracts—which are preventable with early detection and appropriate treatment—can be strong indicators of present or future disease.

Diabetic retinopathy is an eye disease caused by damage to the blood vessels in the retina. It is the leading cause of blindness in working age Americans. Generally, the problem with diabetic retinopathy is that many patients are not aware that they are at risk or even have the disease itself. At first, no symptoms may show, however, this disease can eventually leads to total blindness. Early detection of retinopathy can prevent vision loss.

In addition to diseases relating to the eyes, eye exams may reveal a potential stroke, high blood pressure, diabetes, sexually transmitted diseases, dementia, or even cancer. A convenient eye exam, offering easy physical accessibility that is low or no cost, has the potential to save sight and lives.

SUMMARY OF THE DISCLOSURE

Accordingly, what is needed is a convenient and readily available method and system that may allow for screening for ophthalmic disorders using artificial intelligence and machine learning. In some aspects, a kiosk that may test for the disease located in easily accessible locations may help increase awareness related to the importance of screening and make more people aware of the risks of ophthalmic disease. In some embodiments, an ophthalmic testing system (OTS) may notify users if they may be at risk or in fact do have a range of ophthalmic diseases, such as glaucoma, diabetic retinopathy, or systemic disease.

In some implementations, an OTS may provide general screening to identify the risk level for a patient as it relates to ophthalmic diseases, such as diabetic retinopathy. By using artificial intelligence and machine learning, patients can have immediate, real-time feedback on their ophthalmic and systemic health. Many diseases unrelated to ophthalmic health may have findings that may present in the eyes. Through analysis of characteristics in the retina, an OTS may provide information about a user's general health.

In exemplary embodiments, an OTS may take an image, or a scan, of a patient's retina. The OTS may then rasterize the scan (or cause it to be rasterized at a remote server) into a sequence of one or more dots. The spatial arrangement of these dots may be used as input into an artificial intelligence or machine learning algorithm that can be used to diagnose conditions, to inform the patient of a need to see a specialist, or to train the algorithm to improve its ability to diagnose or inform the patient.

When the scan is "unrasterized" and presented to the patient, relevant portions of the scan may be highlighted to the patient. In this way, the patient can be presented with a visual guide to the patient's retina and can better understand the results of the scan.

BRIEF DESCRIPTION OF THE DRAWINGS

The accompanying drawings that are incorporated in and constitute a part of this specification illustrate several embodiments of the disclosure and, together with the description, serve to explain the principles of the disclosure.

DETAILED DESCRIPTION

Figure 1A:
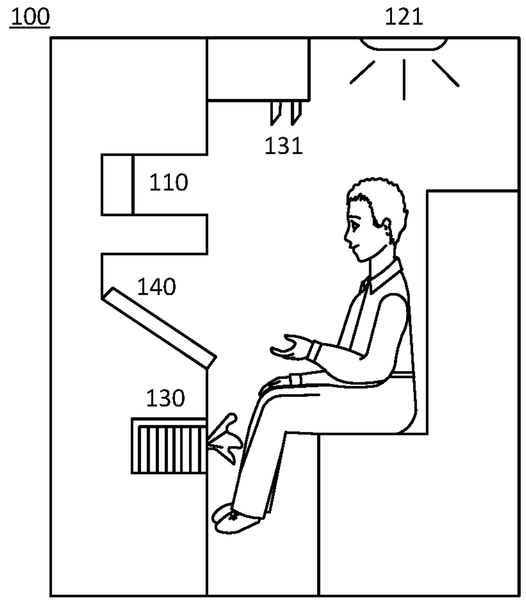
FIG. 1A illustrates a user in a cross section of an exemplary ophthalmic testing system, according to some embodiments of the present disclosure.

The present disclosure provides generally for an exemplary OTS that may prescreen for ophthalmic diseases on demand, without intervention by technicians or other humans. According to the present disclosure, an OTS may screen for disease and other maladies, such as diabetic retinopathy, Alzheimer's, or heart disease, and give the user instant (or nearly instant) results once the test has concluded.

In some embodiments, an OTS may require general and medical information about the user to store and determine more about each test data recorded. In some aspects, an OTS may avoid collecting any data that may trigger HIPAA compliance. In some implementations, limited collection of data may reduce a need for extensive local storage or wireless capabilities for transferring large amounts of data.

In some embodiments, an OTS may process and analyze the ophthalmic images and send them to a user's doctors and healthcare facilities they may have provided. In some implementations, the user may receive instant results from an OTS via a text message or email that the user has provided. In some embodiments, an OTS may print results instantly from the interface for the user to have a physical copy to take to their ophthalmologist. In some implementations, an OTS may process images using artificial intelligence and machine learning. In some aspects, an OTS may use a system that was trained to identify ophthalmic diseases. In some embodiments, an OTS may contribute images to a system to strengthen the OTS's ability to identify ophthalmic diseases.

In the following sections, detailed descriptions of examples and methods of the disclosure will be given. The description of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Glossary

Ophthalmic Testing System (OTS): as used herein refers to a system for screening for ophthalmic disorders, such as age-related macular degeneration (AMD), glaucoma, cataract, diabetic retinopathy, and systemic disorders, as non-limiting examples. In some embodiments, an OTS may capture ophthalmic images of a user's eye, which may be analyzed using artificial intelligence and machine learning to screen for predefined ophthalmic diseases. In some aspects, the ophthalmic images may be analyzed locally, such as through use of artificial intelligence and machine learning algorithms and techniques. In some implementations, an OTS may comprise a standalone kiosk for consumers, such as at a grocery store or drug store. In some embodiments, a health care provider may use an OTS to collect ophthalmic images for a large quantity of patients with limited personnel or staff requirements. In exemplary embodiments, an OTS may include any or all of: a slit lamp microscope, a fundus camera, a non-contact tonometer, a corneal topographer, an auto-keratometer, an autorefractor, and an optical coherence tomography (OCT) apparatus. Although the present discussion will emphasize OCT, any of the foregoing apparatus may be used to obtain similar results.

Referring now to FIG. 1A, a user 150 in a cross section of an exemplary ophthalmic testing system 100 is illustrated. As shown here, ophthalmic testing system 100 comprises an OCT apparatus 110, lighting 121, cleaner dispenser 130, and touchscreen 140. As will be shown later, ophthalmic testing system 100 may also comprise a communications device capable of transmitting and receiving information 131 about the diagnostic test with a remove server.

In some embodiments, the user may use the touchscreen 140 to select diseases they wish to test for from the system and the system may test the user for all selected diseases. In some embodiments, an ophthalmic testing system 100 may test for a particular disease, such as diabetic retinopathy, Alzheimer's, or cardiac disease. In some embodiments, the screening of the ophthalmic testing system 100 may test for a wide range of diseases using the testing device 110 and touchscreen 140, as described herein.

In some aspects, the ophthalmic testing system 100 may prompt the user to input additional information about the user before the test is performed. In some implementations, this information may help determine what tests the user may need to take. In some embodiments, the system may simply recommend the specific tests the user may need to be screened for and it may be up to the user's discretion whether they take the recommended tests or not. For example, if a user inputs that they have diabetes, the OTS 100 may suggest screening for diabetic retinopathy, or if a user inputs that they are older than 65, the OTS 100 may suggest screening for glaucoma. If input of general information does not present an immediate risk for a known ophthalmic disease, an OTS 100 may allow for manual selection of the screening.

In some embodiments, ophthalmic testing system 100 may transmit the user-inputted information to a remote server. The remote server may provide additional recommendations based upon observed data. For example, if a significant proportion of ophthalmic testing systems in a geographic region showed that people over the age of 60 were more likely to have glaucoma than people over the age of 60 in other regions, then the remove server may prompt ophthalmic testing system 100 to screen for glaucoma.

In some implementations, the ophthalmic testing system 100 may require the user to enter information protected by the Health Insurance Portability and Accountability Act (HIPAA) such as, by way of non-limiting example, name, birthday, and insurance. In some implementations, the information gathered by the ophthalmic testing system 100 may be entered by the user on the touch screen 140 to be recorded in the system. In some aspects, the ophthalmic testing system 100 may use the information provided for collection of screening data to be distributed to a doctor or healthcare facility for further examination. In some embodiments, ophthalmic testing system 100 may use this information for personalization of the services and to confirm insurance payment, and then delete that information.

In some implementations, the ophthalmic testing system 100 may have a memory system incorporated, which may allow for user information to be stored. Storage of data may be temporary and may be deleted periodically, such as daily or when a threshold amount of data is stored. In some embodiments, an OTS 100 may periodically transmit data to an external database, such as to a healthcare provider or a health database for the OTS 100, as non-limiting examples. In some implementations, a health database for the OTS 100 may be accessible to users, healthcare providers, and research analysts, as non-limiting examples. Accessibility may be limited based on the entity. For example, a user may be able to access their personal data, healthcare providers may access the data related to their patients, and research analysts may have access to all of the general data scrubbed of any personal or identifying data. In some aspects, the system may limit the user to inputting non-identifying data to avoid any HIPAA requirements similar to that of a blood pressure kiosk at a store.

Ophthalmic testing system 100 may further include sensors allowing for the detection of other data relating to the patient. This data may be useful for correlating with data obtained from the patient's retinal scans. For example, ophthalmic testing system 100 may include a global positioning system (GPS) to allow for geographic coordinates to be appended to the patient's retinal scan. Additionally, ophthalmic testing system 100 may include a scale, a height measurement, a pulse oximeter, a pulse reader, a blood pressure cuff, or any other sensors descriptive of a health condition of the patient.

Figure 1B:
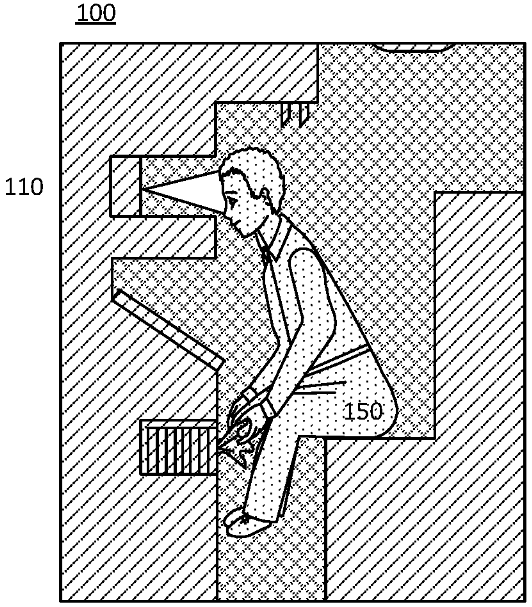
FIG. 1B illustrates a user in a cross section of an exemplary ophthalmic testing system, according to some embodiments of the present disclosure.

Referring now to FIG. 1B, a user in a cross section of an exemplary ophthalmic testing system 100 is illustrated. In some embodiments, a darkening mechanism may enclose an OTS 100 as shown and keep all light out of the interior of the system. In some implementations, the lighting 121 may be controlled before and after the system has concluded the tests on the user. In some aspects, the lighting 121 may be turned on and off when the darkening mechanism is still active. For example, the darkening mechanism may be blocking out all the light from the system but the lighting 121 may still provide illumination inside an OTS 100.

As shown in FIG. 1B, user 150 is leaning in for imaging from an OCT apparatus 110. OCT apparatus generally uses light waves to take cross-section pictures of the user's retina. The process of taking such pictures is shown in more detail in FIG. 2.

Figure 2:
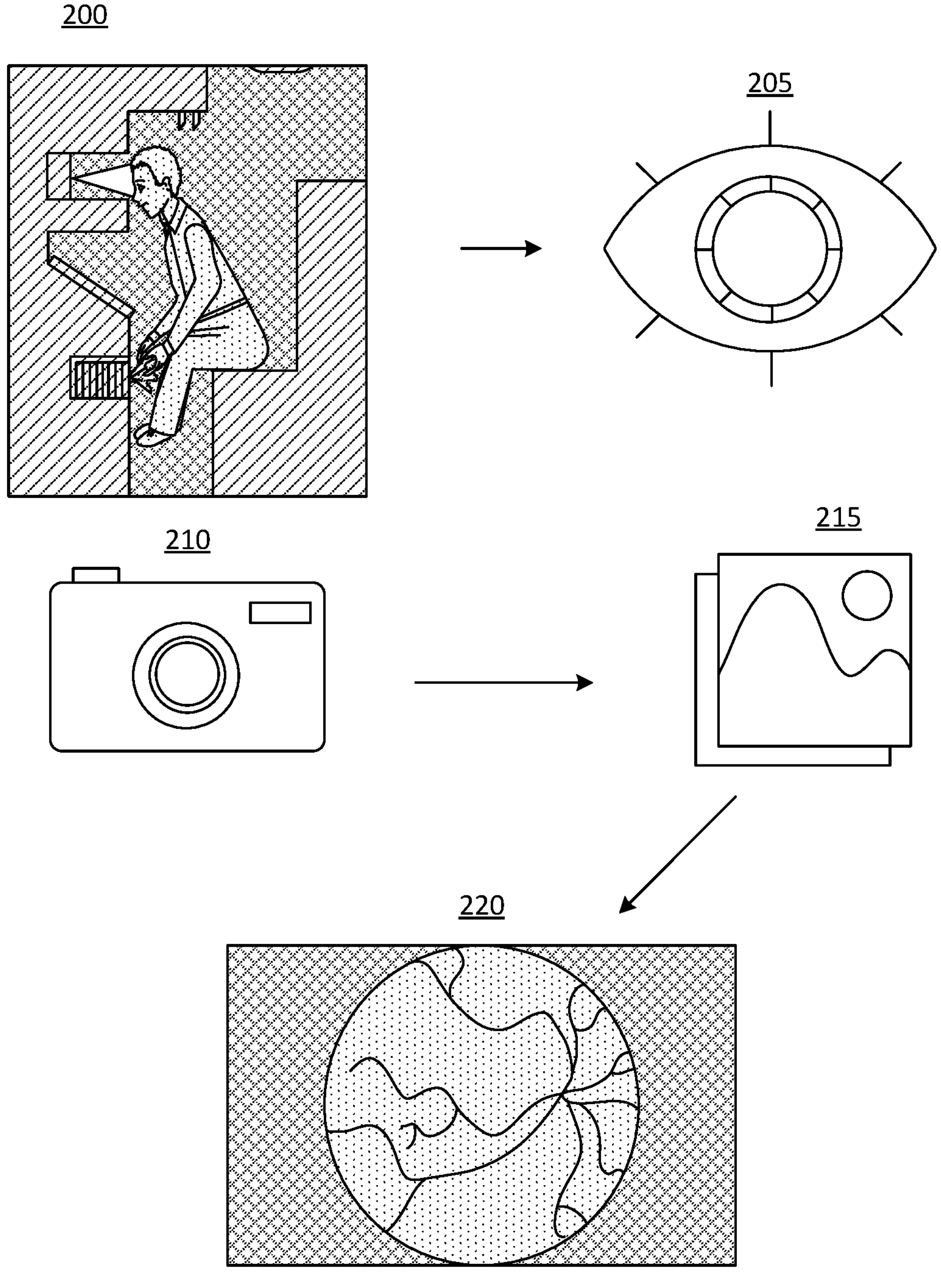
FIG. 2 illustrates exemplary process steps for capturing an image of the eye, according to some embodiments of the present disclosure.

Referring now to FIG. 2, exemplary process steps for capturing an image of the eye is illustrated. In some aspects, at 200, a user may sit down at the kiosk to be instructed for further examination. In some aspects, the user may be prompted different instructions based on their height, weight, medical issues, and other non-limiting examples. The ophthalmic testing system 100 may automatically, or through user input, adjust the height and depth of the imaging apparatus (e.g., an OCT apparatus) as needed to capture an image of the user's retina. Once the user has set up the device properly, the user can place the user's eye at a location proximate to the imaging apparatus 205. At 210, the imaging device may begin scanning the eye to create an image 215. The retinal scan 220 may then be transmitted through the system. In some embodiments, the OCT device may determine that the scanned image is inconclusive, such as based on the presence of occlusions like eyelashes, user movement, improper lighting, etc. In that case, the user may be prompted to retake the image.

Once an image of sufficient quality is obtained, then the image is then examined microscopically by the system to determine the issues, if any, with the eye of the user. In some embodiments, the image may be rasterized into a series of pixels, dots, or lines. (In some embodiments, it may be necessary first to convert the scanned image to vector data.)

In some aspects, the system may use previously generated images to compare the captured images of the patient to identify possible issues with the retina. In some embodiments, the system may use an algorithm to identify specific areas of the image and help discern patterns so that the system recognizes potential issues faster in the future. In some implementations, the images may be saved as a copy into the system for future reference, or used to recover if physical copies are lost. In some aspects, the system may pull these generated images from a web browser or the system may have manually generated images generated into the system when searching with similar images. In some embodiments, the system may compare the image (or the rasterized version thereof) to ascertain the existence of anomalies relative to a group of preloaded images that characterize retinas of "normal" status or retinas showing certain conditions (e.g., glaucoma, macular degeneration, diabetes, etc.)

Figure 3A:
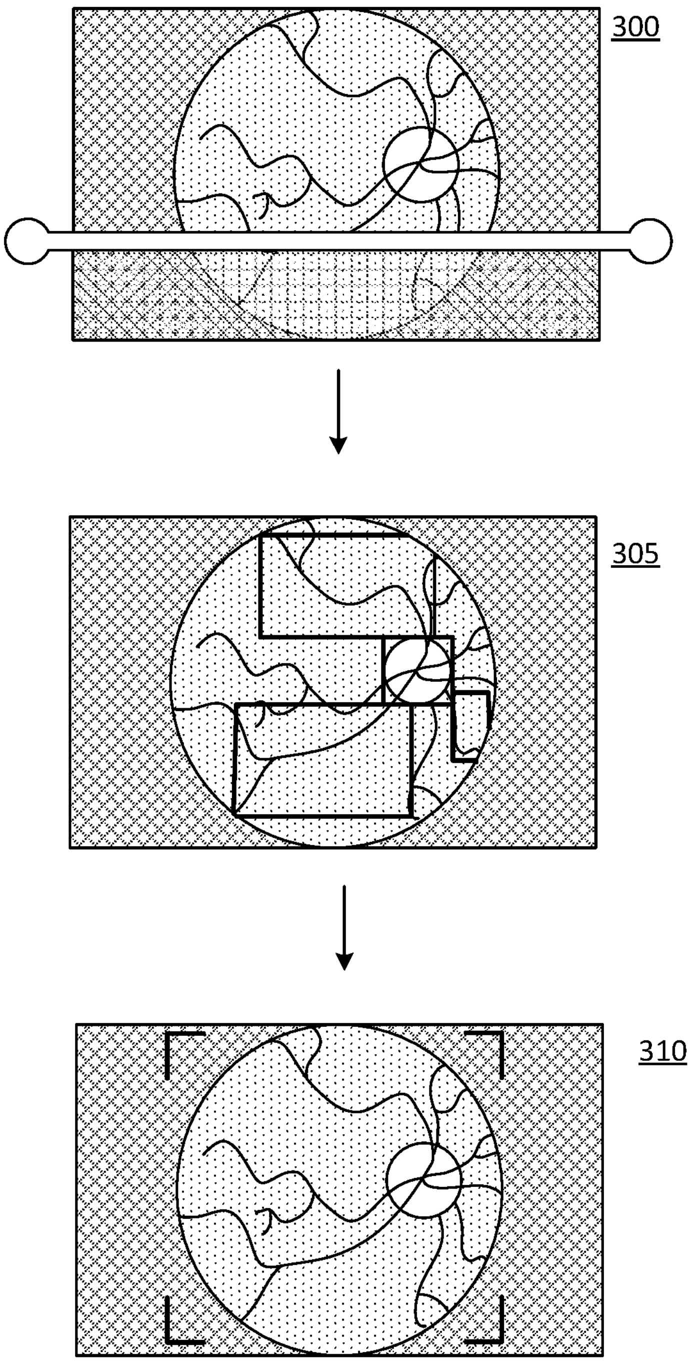
FIG. 3A illustrates exemplary image analysis steps for processing an image of the eye, according to some embodiments of the present disclosure.
Figure 3B:
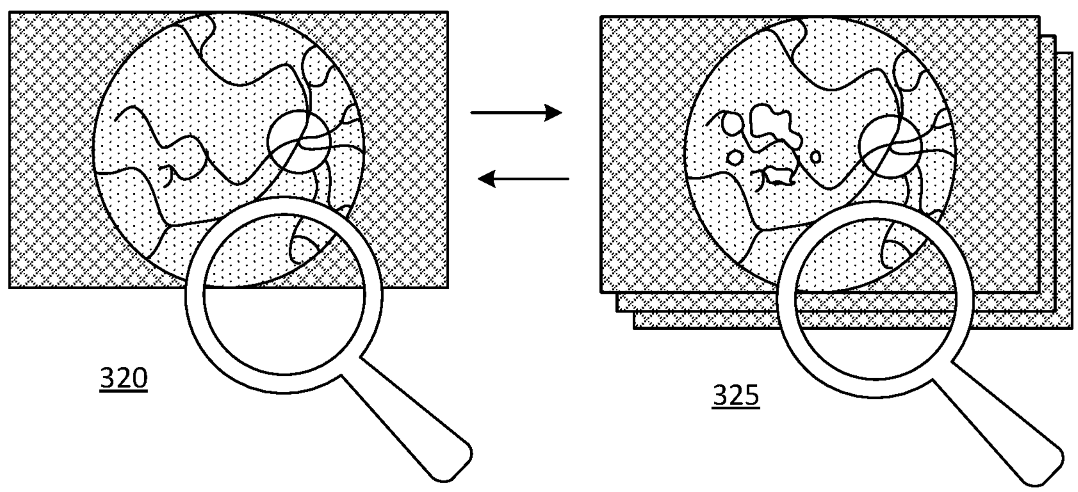
FIG. 3B illustrates exemplary image analysis steps for processing an image of the eye, according to some embodiments of the present disclosure.
Figure 3C:
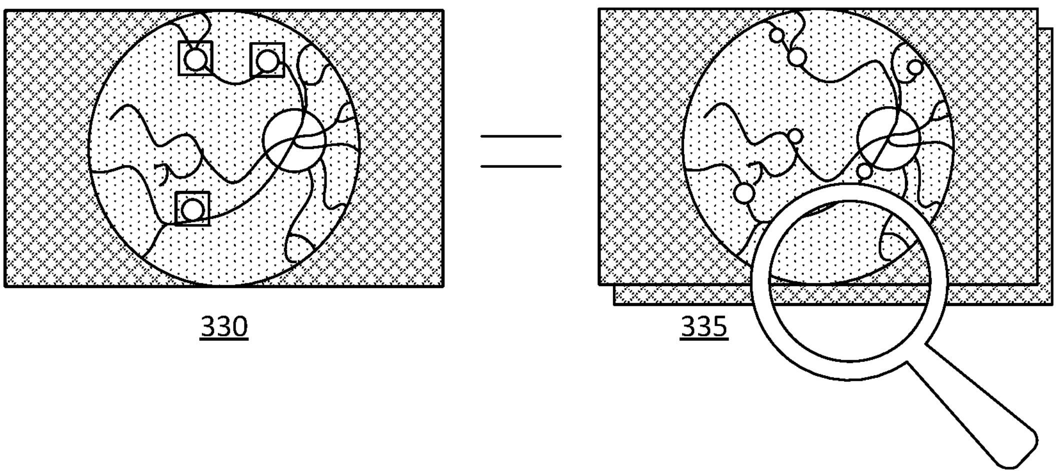
FIG. 3C illustrates exemplary image analysis steps for processing an image of the eye, according to some embodiments of the present disclosure.

Referring now to FIGS. 3A-3C, exemplary image analysis steps for processing an image of the eye are illustrated. Some or all of these steps may be practiced in connection with a given type of diagnosis. For example, in FIG. 3A, 300 illustrates the process of rasterizing an image into small pixels or subregions. Similarly, 305 shows a method focused on detection of key features, such as the inner retina and blood vessels. And 310 shows an image focused on the retina as a whole. As shown in FIG. 3B, a zoom feature 320 can create a zoomed image 325 for further study.

In some aspects, the image may be captured by the system and then uploaded to a remote server to be further analyzed, while in other implementations, the image may be analyzed on the system itself. In some implementations, algorithms may then be used to help single out specific areas in an image. In some implementations, the system may target specific areas within the image or it may scan the entire image as a whole.

In some aspects, the image may be cross referenced with other images located in the system, such as training data that may be used in generating an artificial intelligence and machine learning algorithm. In some embodiments, the system may use an algorithm to cross reference these images that may be related to the unique image of the retina of the user. In some aspects, the system may take various amounts of time to determine if the image is compatible with other images. In some embodiments, if the image is not able to be cross-referenced within the system and then may need to be uniquely examined by the system. In some implementations, if the image is unique to the system, then the system may then generate an algorithm to save that unique image for future examinations. For example, as shown in FIG. 3C, certain highlighted features on the retinal scan 330 can be overlaid with images for cross-referencing at 335 and studied to ascertain the presence of abnormalities. These abnormalities may be indicative of disease.

In some embodiments, the system may then find matches for the image of the patient and images integrated within the system. In some aspects, there may be more than one image that helps identify possible issues with the patients' retina. For example, one image may have a similar section to the retina image but not completely match the rest of the image, however, the AI may select an image that matches the rest of the image of the patient that was taken. In some aspects, the different images generated by the algorithm of the system may be combined into one composite retina indicative of a healthy condition or of a potential abnormal condition. For example, the rasterization process may convert an image into a series of dots or pixels. Patterns of these pixels can be analyzed to assess similarities between, for example, the patient's retina and the pixel pattern associated with a scan of a patient with a cataract diagnosis. In this way, the patient's retinal scan can be used to identify potential maladies.

For example, the presence of cataracts may be indicative of a future disease. This is in part because cataract surgery has been linked to future exposure to cardiac disease. Cortical cataracts are associated with Alzheimer's disease. These may appear as opacities in what should otherwise appear to be clear portions of the lens. Similarly, dry macular degeneration can be evidence of potential oncoming Alzheimer's disease in a patient.

Relatedly, by cross-referencing scans of a patient's retina with older scans of the patient's retina, the thickness of the patient's retinal nerve fiber layer can be monitored over time. A decrease in the thickness of this retinal nerve fiber layer has been linked to glaucoma and Alzheimer's disease as well.

Figure 3D:
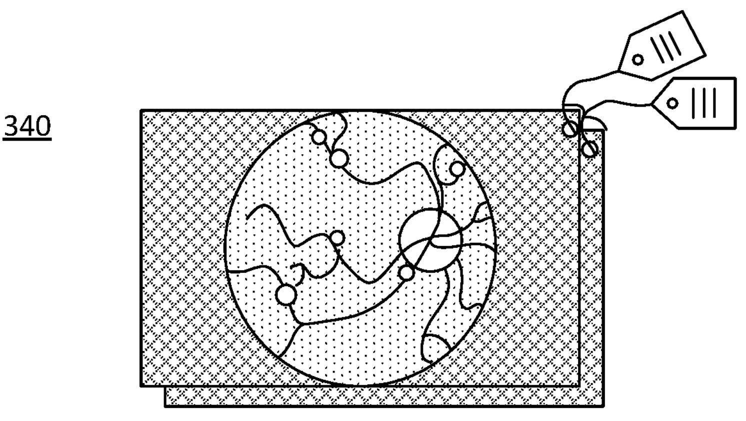
FIG. 3D illustrates exemplary image tagging steps for processing an image of the eye, according to some embodiments of the present disclosure.
Figure 3E:
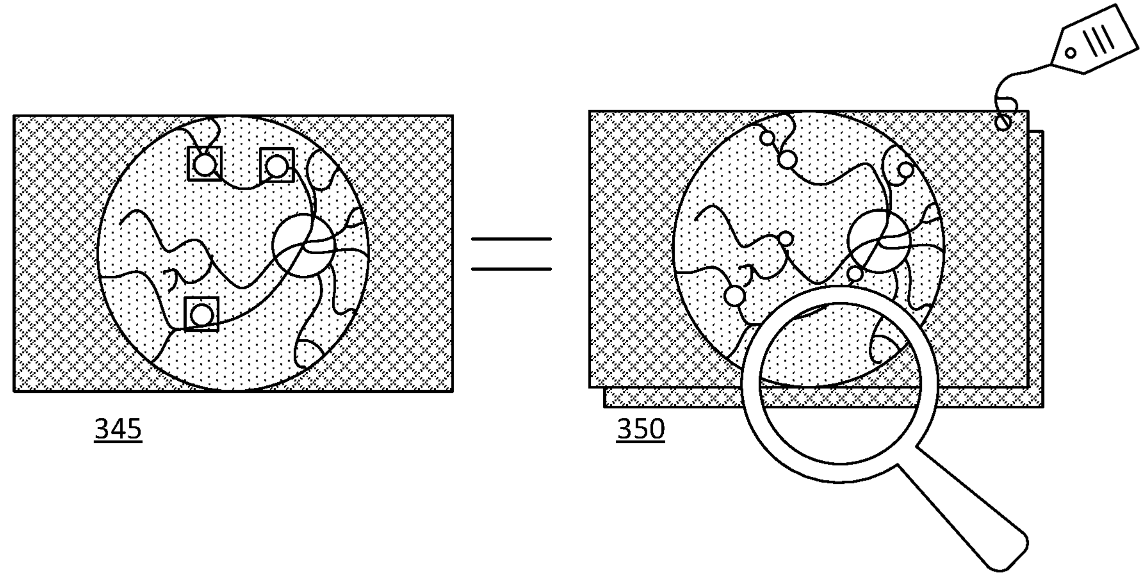
FIG. 3E illustrates exemplary tagging steps for processing an image of the eye, according to some embodiments of the present disclosure.
Figure 3F:
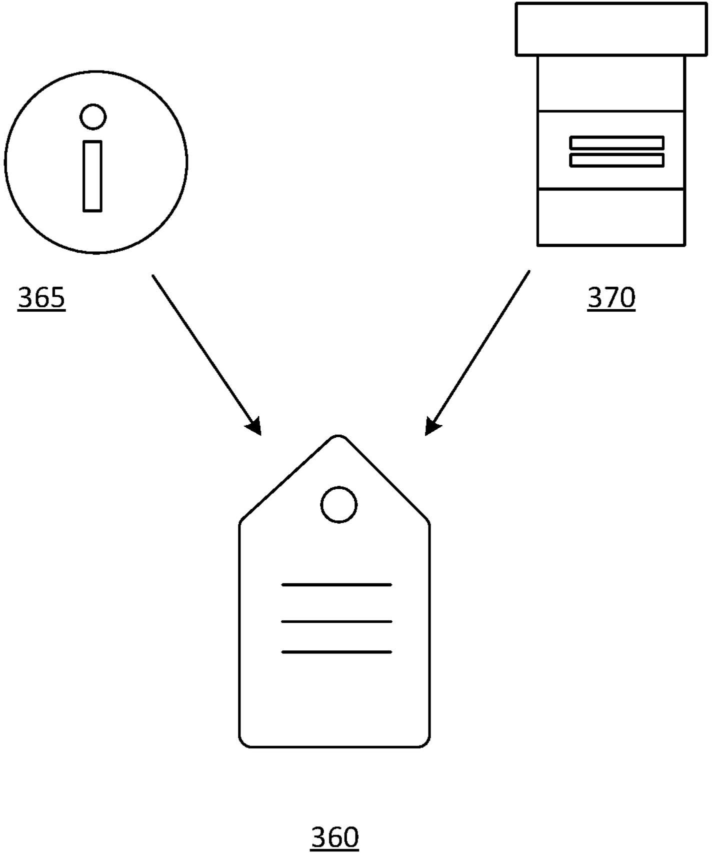
FIG. 3F illustrates exemplary tagging steps for processing an image of the eye, according to some embodiments of the present disclosure.

Referring now to FIGS. 3D-3F, exemplary image tagging steps for processing an image of the eye are illustrated. First, the image is taken by the system using the camera and then processed through the system. As discussed above, the camera may be an OCT apparatus, a fundus camera, a slit lamp microscope, or any other apparatus capable of imaging a retina. The system then processes microscopic areas of the image to the identify patterns and raise other areas of concern throughout the system. In some aspects, the system may not recognize or identify any patterns but continue to examine the image more than once to ensure the system identifies any possible outcomes. These microscopic areas may be represented by one or more patterns of pixels obtained from one or more rasterization processes of the retina scans. In some embodiments, these areas may also be detected through other algorithms, such as edge detection and Fourier transformers.

In some aspects, the AI of the system may then generate specific tags for each image based on their information and possible classification of health issues, as shown in 340. In some implementations, an algorithm may generate unique tags for each image based on various different non-limiting examples that help classify the image. In some embodiments, the image tags may not be mutually exclusive, however, one image may have a tag that another image may not have. In some aspects, the AI of the system may help store and distribute the images taken of each patients' retina. For example, there may be a cloud storage system within the AI that permanently stores all images. In some implementations, the images may be deleted at any time.

The tags may relate to any number of characteristics that may be desirable for subsequent database queries. For example, a scan may include data such as the patient's age, sex, weight, height, medical history, or geographic location. This may be useful in subsequent scans: a patient seeking general comparative information about the health of their eye may wish to obtain a more apt comparison by obtaining results comparing the patient's retinal scan results with those of someone having similar characteristics.

Moreover, after a scan, if it is determined that the retina reflects certain adverse conditions, then the tags may be updated accordingly. For example, a retina scan reflecting macular degeneration may then be tagged with an indicator that the scan reflects potential macular degeneration. This may be useful for comparing subsequent scans of the retinas of other patients. For example, if the patient is concerned about their own macular degeneration, then the patient's retina scan may be compared with the scans tagged as potentially showing macular degeneration.

Once the image has been scanned the system may go through each area that has been identified as a possible area of interest or possible health concern. The system may then take note of the area and tell the system what, if anything, is wrong with that area of the image. Once each image has been examined it is then tagged with the information the system has processed for that image. Each image may have its own tag, and relate each tag to another image if a different image has a similar pattern or relates to a preexisting health condition that the user mentioned.

Similar images may be compared on the system and related as previously stated through similar tags or linked on the same screen next to the other similar photos, as shown in the comparison between 345 and 350. Once all photos have been assessed and tagged by the system then, the photos may then be quickly processed and scanned a second time to ensure nothing has been missed and all areas of each photo have been assessed and discussed in the findings. In some embodiments, this may proceed by comparisons to additional photos to ascertain key diagnostic components, such as blood vessels. After the second scan through the system then collects all the information and tags and complies it into a results folder. The results are then processed by the system and then may be printed at for the user and/or sent to their healthcare provider for further inspection.

In some embodiments, the results may be displayed on the touchscreen or on another monitor. The results may be annotated for the user's convenience. One way this can be done is to "derasterize" the images to create vector images. In some embodiments, these vector images may be colored or highlighted. For example, compared portions of the respective retinal scan images (e.g., blood vessels, vitreous) may be highlighted to show the user a rationale for a particular diagnosis. For example, if the user's retinal scan shows a thinner or cloudier vitreous, and a baseline scan of a patient having cataracts shows a similar quality of vitreous, then the user's retinal scan may be shown alongside the scan of the cataract patient to highlight the nature of the vitreous. In some embodiments, this may also be compared to a scan of a patient with a healthy eye to demonstrate what non-cataract vitreous looks like.

Additionally, as shown in FIG. 3F, a tag 360 may be updated with additional information 365. For example, in a given geographical region, it may be that a statistically significant number of patients present with blood vessels having a different quality than previously noticed. Based upon such an observation, an additional tag 360 may be created—or a preexisting tag may be updated—to allow the OTS to monitor for blood vessels having that quality. This may be reflected in the rasterized dots of a scan corresponding to the blood vessels. New diagnoses or proposed treatments 370 may also be appended to the tag to assist the patient in treating any conditions correlated with the updated information. Accordingly, by way of nonlimiting example, if patients in Northeast Florida begin having scans showing clots of pixels in the rasterized images of the blood vessels in the retina, and a disproportionate number of cardiac events begin happening in Northeast Florida, then diagnoses 370 may suggest to a patient showing similar blood vessels that the patient should seek cardiac screening.

Figure 4A:
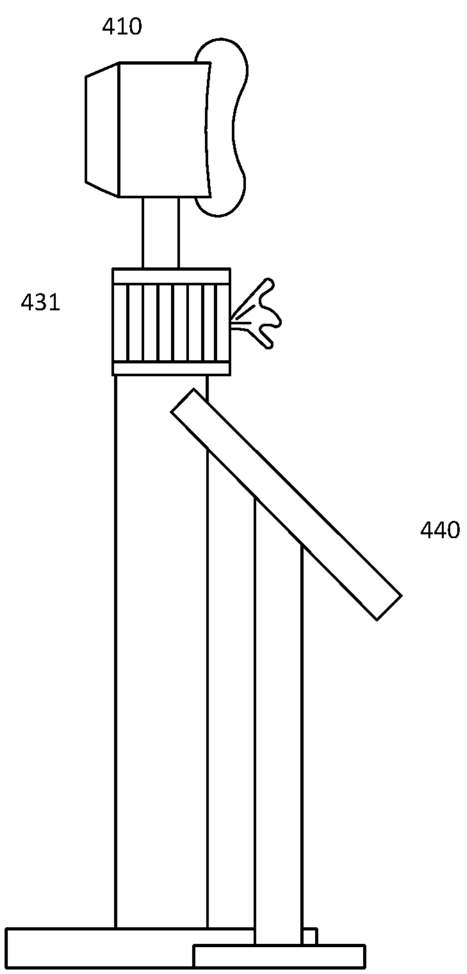
FIG. 4A illustrates an exemplary ophthalmic testing system, according to some embodiments of the present disclosure.

Referring now to FIG. 4A, a side view of an exemplary ophthalmic testing system 400 is illustrated. In some embodiments, the ophthalmic testing system 400 may be set up where the testing device 410 may be set up on a stand. In some embodiments, the testing device 410 act as a darkening mechanism within an OTS 400 to ensure the testing device 410 is not exposed to any light.

In some embodiments, a touchscreen 440 may be a separate entity from the testing device 410. In some implementations, the touchscreen 440 may be attached to the testing device 410 to provide a more fluid process when a user is being prompted, such as illustrated in FIG. 4C. In some aspects, the touchscreen 440 may be mobile so the user may be able to hold it while directed through the process. For example, the user may hold the touchscreen 440 in one hand while setting up the testing device 410 rather than look back and forth from the two entities and possibly miss an important prompt from the system.

In some embodiments, cleaning wipes 431 may be located below the testing device 410. In some implementations, a holder may be attached to a surface below the testing device 410, wherein the holder may secure the cleaning wipes 431. For example, the cleaning wipes 431 may come in a separate box or case and the holder may secure the cleaning wipes 431 inside and hold them for use before and after the ophthalmic testing system 400 has been used.

In some aspects, the touchscreen 440 may have a wireless interface connected to the ophthalmic testing system 400, which may allow for relay of all information and results between the two entities. Additionally, touchscreen 440 may include controls for activating image capture devices within testing device 410, such as an OCT apparatus.

As discussed above, OTS 400 may further include sensors to obtain additional information descriptive of the patient's health, such as height, weight, pulse, blood pressure, and the like. Moreover, OTS 400 may include a communications device. This may be useful to allow low-powered OTS 400 to be deployed in multiple locations, and for one or more complex calculations to occur at a server remote to OTS 400. For example, if OTS 400 primarily collects sensor and imaging information, OTS 400 may then transmit that information to a remote server for the analysis and comparison tasks discussed herein, such as the rasterization of the images and comparison of the images.

Figure 4B:
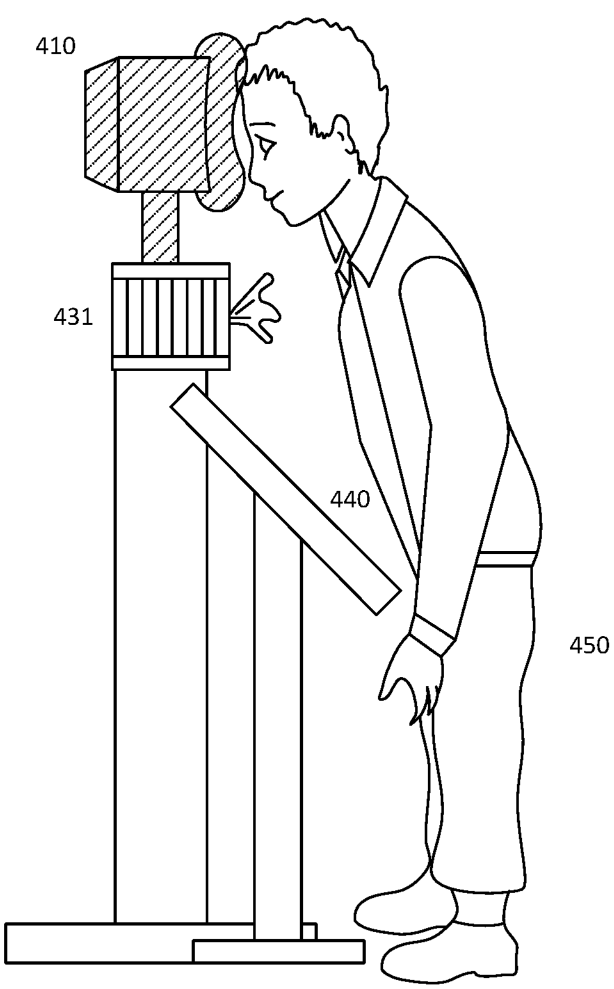
FIG. 4B illustrates an exemplary ophthalmic testing system, according to some embodiments of the present disclosure.
Figure 4C:
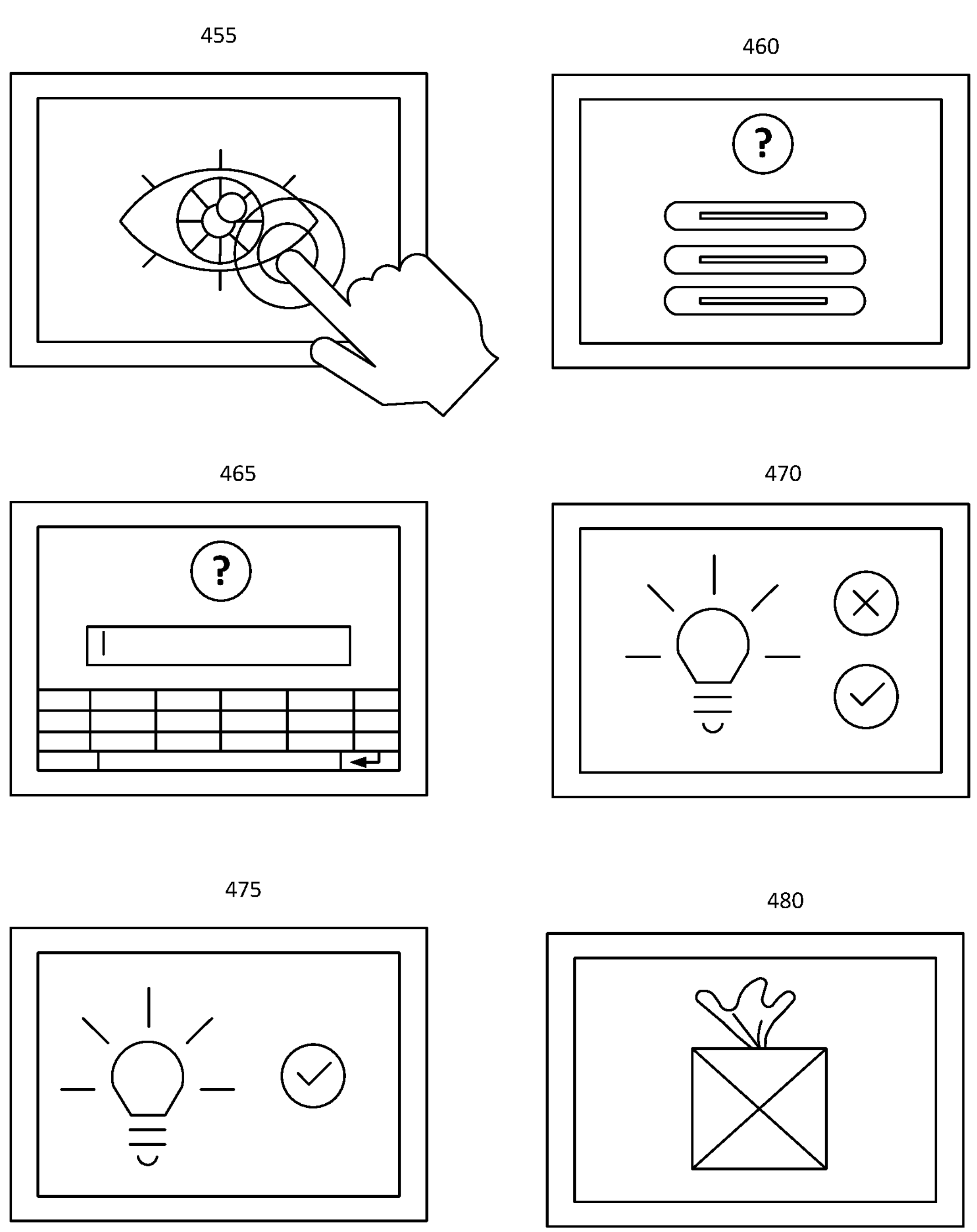
FIG. 4C illustrates exemplary user interfaces for an ophthalmic testing system, according to some embodiments of the present disclosure.

Referring now to FIG. 4B, a user 450 in a side view of an exemplary ophthalmic testing system 400 is illustrated. In some embodiments, the user 450 may lean into the ophthalmic testing system 400 as shown for proper use. In some implementations, the user 450 may adjust the height of the ophthalmic testing system 400 to their preferred height for comfort and accuracy. In some aspects, the user 450 may require a chair to sit and use the ophthalmic testing system 450, wherein the user 450 may adjust the device to the height of their chair.

In some implementations, a third party may assist or guide a user through the use of the OTS 400. In some aspects, the third party may set the height, may direct the user how to position themselves for the screening, and may monitor the testing to ensure the environmental conditions will produce accurate results. In some embodiments, OTS 400 may be primarily or entirely self-administered, thus allowing for greater deployment possibilities.

In some embodiments, the ophthalmic testing system 400 may have another display screen on the inside of the testing device 410 that may relay the same screen as the touchscreen 440. In some implementations, the display screen on the inside may be viewed by the user 450 while using the testing device. For example, the touchscreen 440 may prompt the user 450 to begin using the testing device 410 and the user 450 may follow the rest of the prompts from the interior of the testing device 410 using the display screen rather than continuously pull their head out and look at the touchscreen 440. In some embodiments, the display screen may prompt the user 450 to correctly sanitize the testing device 410. In some aspects, the touchscreen 440 may be controlled by a third party, such as a healthcare provider. In some embodiments, if the imaging device is unable to capture a sufficiently definite image of the user 450's retina, then the imaging device may transmit a signal to touchscreen 440 prompting the user 450 to correct one or more of: the height of the ophthalmic testing system 400, the stance of the user, the hair of the user, or the blinking patterns of the user.

Referring now to FIG. 4C, exemplary user interfaces for an ophthalmic testing system 400 are illustrated. In some embodiments, the user 450 may prompt the device by touching it to start 455. In some implementations, the touchscreen 440 may be at rest before the user 450 presses on the screen to start the process. Once the interface has been activated, the OTS 400 may transmit general questions 460 about the user. For example, the general questions 460 may relate to known risk indicators associated with predefined ophthalmic diseases, such as pre-existing conditions, age, or weight, as non-limiting examples. In some aspects, user responses may determine relevant screening tests for the user. In some embodiments, the screening test types may be set by a third party, such as a healthcare provider or clinic.

In some implementations, the user 450 may be prompted to enter their information regarding the questions asked by the interface. The OTS 400 may prompt input of contact information 465, which may allow for transmission of results to the user. In some embodiments, the contact information 465 interface may further prompt the user 450 for more detailed information, which may be used by the healthcare provider for their records. In some aspects, the user 450 may choose if they want to be contacted via email or phone number. For example, there may be a prompt which the user 450 may select whether they want to input their phone number or email address. In some embodiments, input of contact information 465 may be optional or may be limited to information that may allow for adequate data tagging, which may be integrated into the training data for the artificial intelligence that provides results to the user 450.

In some embodiments, the interface may prompt the user 450 to begin testing 470. The user 450 may be prompted to turn the lights off, and the test may be starting after the lights are turned off within the testing device 410. In some embodiments, one or more of these prompts may include tactile feedback for the user, to allow the user to focus on proper eye placement rather than on touchscreen manipulation. Once the user 450 has pressed the begin test button 470 (which may be a digital or a physical button), the interface may rest while the test is being performed. In some aspects, the OTS 400 may indicate when an effective test is complete 475. In some implementations, the interface may instruct the user 450 how to clean the device 480 after it has been used.

Figure 5A:
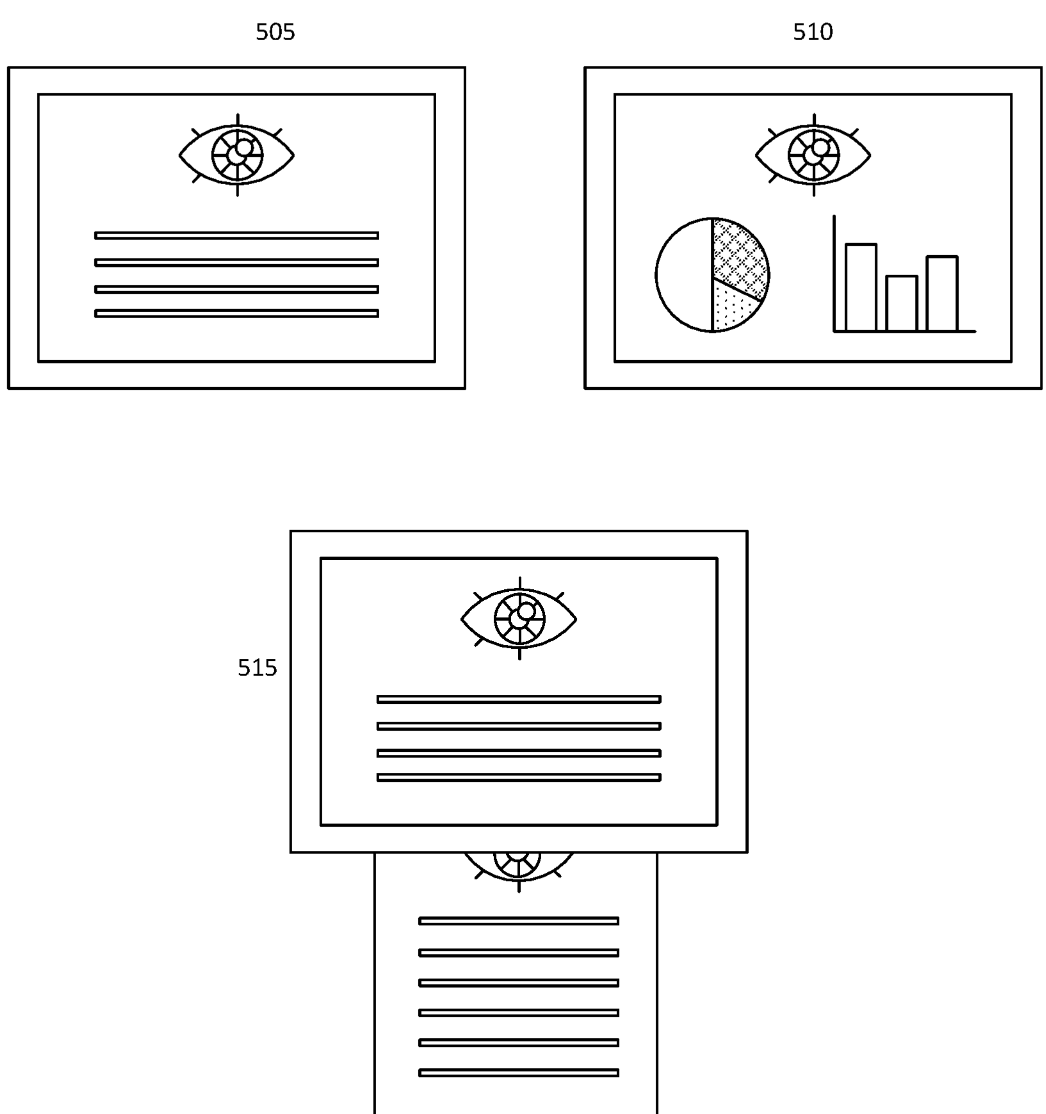
FIG. 5A illustrates exemplary results user interfaces for an ophthalmic testing system, according to some embodiments of the present disclosure.

Referring now to FIG. 5A, exemplary results user interfaces for an ophthalmic testing system are illustrated. In some embodiments, the interface may display the results on the screen as text 505 or pictorially 510. In some aspects, the interface may prompt the user to select whether they want the information emailed to them or sent to their phone. In some embodiments, the user may print their results 515. In some implementations, results may be presented by risk level, such as low, medium, or high risk. In some aspects, the immediate results may be processed automatically, such as based on artificial intelligence and machine learning algorithms. Providing risk levels may limit liability for providing inaccurate results, such as may occur when performing fully automated testing and review.

In some embodiments, the ophthalmic testing system may make an initial determination of a primary risk factor. Based upon a cross-reference to a database, the ophthalmic testing system may make a correlation between the primary risk factor and a secondary disease risk. For example, the presence of cataracts—and the subsequent need for surgery—has been linked to an increased risk for cardiac disease. Accordingly, a determination of a primary risk factor (such as the presence of cataracts) may lead the ophthalmic testing system to output to the patient that the patient is at risk for cardiac disease.

In some embodiments, the user may be presented with results that they may be able to provide to their healthcare provider. In some implementations, test data may be stored, wherein the data may be organized by personal identifier or by anonymous tagging. Where the test data may be organized by anonymous tagging, a user's results may not be accessible based on their name or other personal information, and the data may be packaged by a tag, such as QR code, randomly generated serial number, or other identifying mechanism. This may limit HIPAA compliance requirements for the OTS and allow for a healthcare provider to access the collected health data.

In some embodiments, the interface may send the results to a doctor's office or healthcare facility the user may have provided to the interface. In some implementations, the interface may prompt the user if they wish to have their results printed out despite them providing their email address or phone number in the previous stages. In some aspects, the interface may not require any additional information from the user based on their previous selections and may only display the results for an allotted amount of time and notify the user that the result may have been sent to their preferred contacted.

Figure 5B:
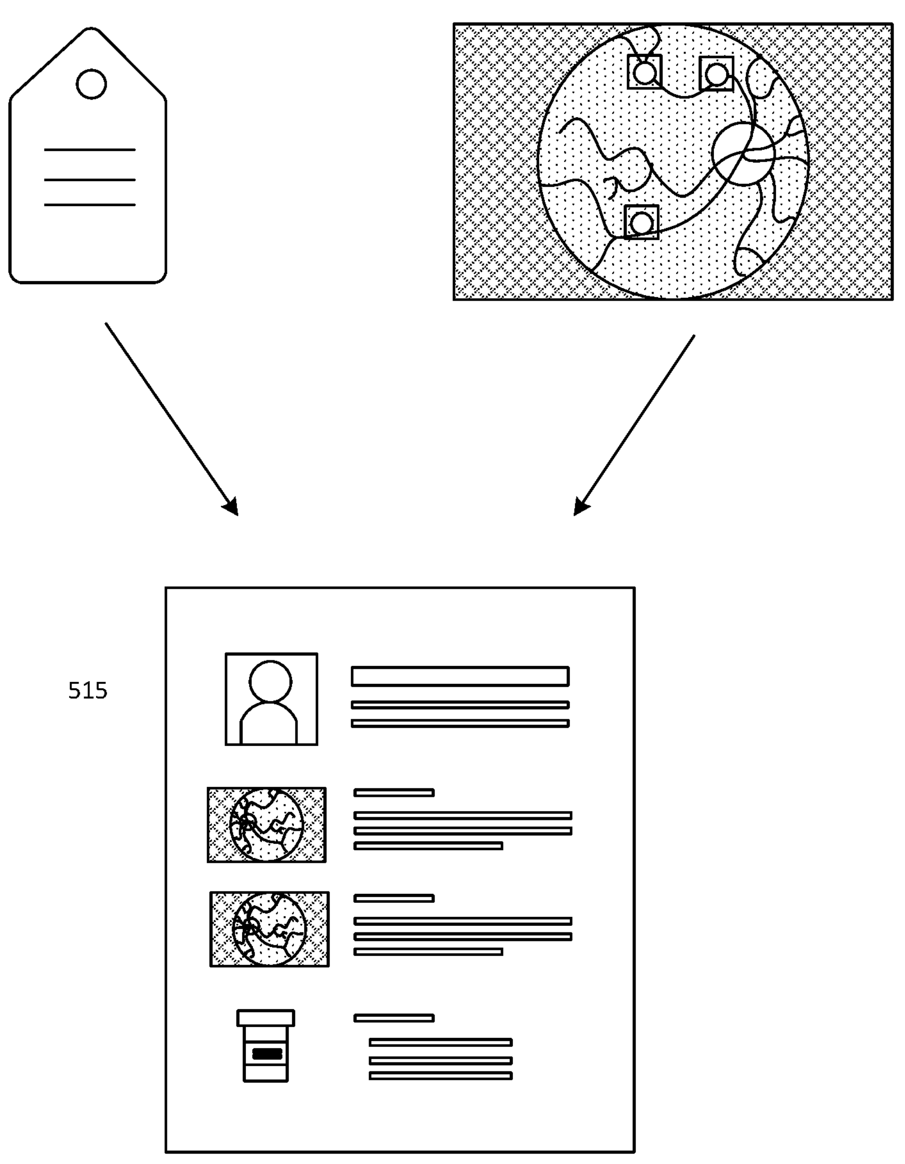
FIG. 5B illustrates an exemplary results user interface for an ophthalmic testing system, according to some embodiments of the present disclosure.

Referring now to FIG. 5B, an exemplary results 515 user interface for an ophthalmic testing system is illustrated. In some aspects, the user may elect to put the entirety of their results onto the print out, however, they may elect to refrain from putting certain information on the results page. In some implementations, private health information may be hidden or left off of the results if chosen to do so by the user. In some embodiments, the results for each patient may vary based on their test results and images. In some implementations, more than one patient may have similar results because of their medical histories, symptoms, and other non-limiting examples.

In some aspects, the results may feature the images taken, but in a different manner than they were examined by the system. For example, a larger, less clear image may be displayed on the results highlighting the issues in the image for the user to see for themselves and help them visually understand the issues. In some implementations, the results may be sent electronically to the user through an email or application linked to the device. In some embodiment, the results may be printed out and electronically sent in the event that the user were to lose their printed version. In some aspect, the electronic version may reveal more information than the physical copy because it is private and may require some sort of access code.

Similarly, as described above, a de-rasterized, highlighted, or annotated version of one or more of the user's retinal scan and a comparison image may be presented to the user to educate the user on particular risk factors. In this scenario, the results may include these de-rasterized, highlighted, or annotated images.

In some aspects, the results may be sent to the users' healthcare provider as well as a physical copy printed for their use. In some implementations, the healthcare provider may use these results to further their diagnostic of the user. In some aspects, the results may be saved on the device's database in the event that the a copy is never received by the user or anyone else that the results may be sent to. For example, if the user were to lose their physical copy and no electronic copy was sent then the user may contact the manufacturer or customer service to receive their results via email or mail. In some implementations, the results may not be limited to a certain length of pages or words. For example, the results may encompass all information, images and any other relevant aspects related to the users' results. These results may be accessed through HIPAA-compliant means, such as the issuance of a PIN number to the user.

Figure 6:
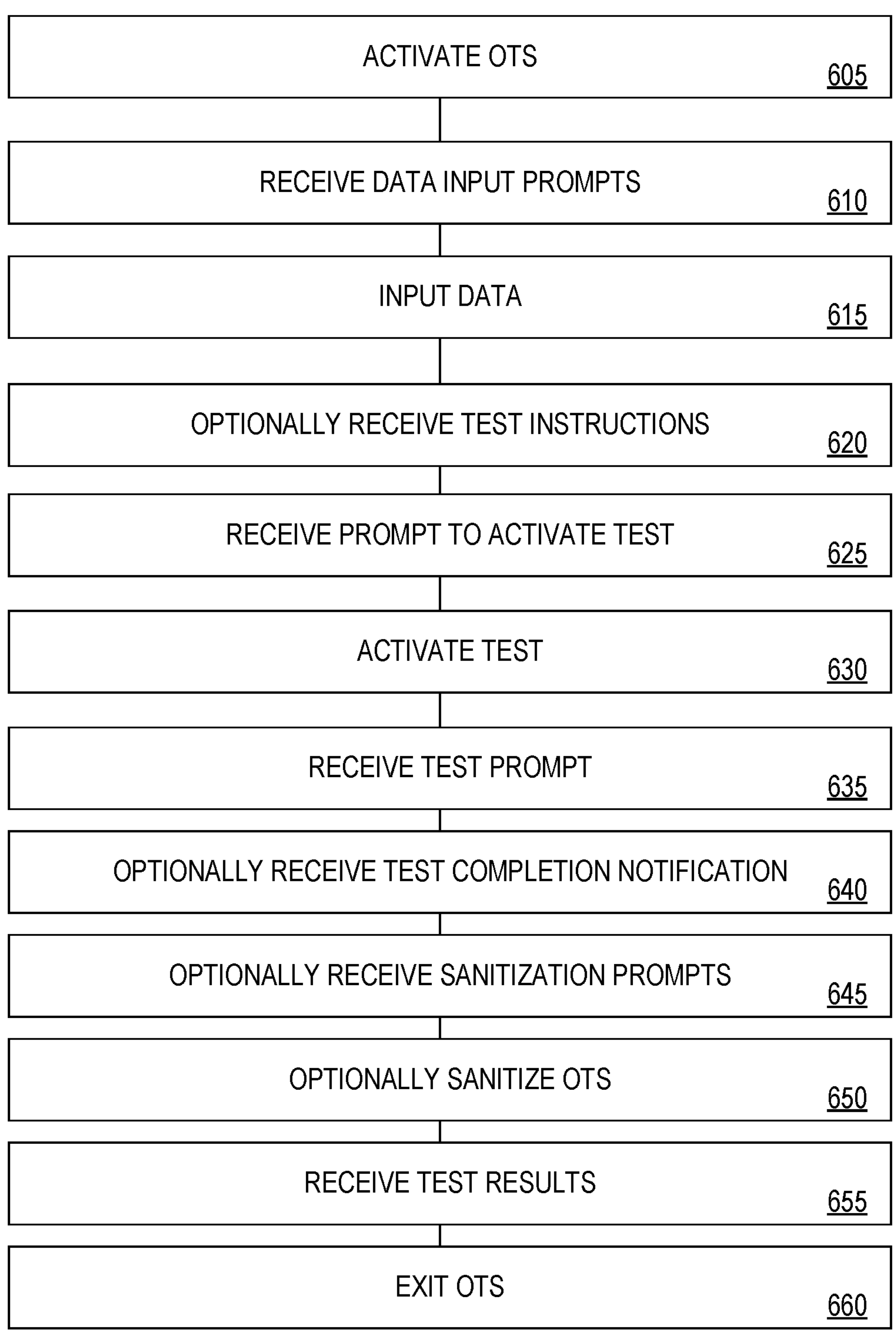
FIG. 6 illustrates exemplary method steps for using an ophthalmic testing system, according to some embodiments of the present disclosure.

Referring now to FIG. 6, exemplary method steps for using an ophthalmic testing system are illustrated. At 605, an OTS may be activated. At 610, data input prompts may be received. At 615, data may be input. In some aspects, the data input prompts may comprise general health data, which may be used to guide the types of ophthalmic tests. In addition to the input prompts, additional data may be obtained through sensors on the ophthalmic testing system, such as a scale, blood pressure cuff, and the like. In some embodiments, at 620, test instructions may be received, such as explanations, directions for set up, particular conditions for diagnosis, or test information, as non-limiting examples.

At 625, a prompt to activate test may be received. At 630, testing may be activated. This testing may be activated by the user's interaction with the prompt. In some embodiments, this prompt may include tactile feedback to allow the user to position the user's eye proximate to an image capture device, such as an OCT apparatus. At 635, test prompts may be received, such as closing one eye, blinking, or looking at a specific point, as non-limiting examples. In some implementations, at 640, test completion notification may be received. In some embodiments, at 645, sanitization prompts may be received, such as "wipe down surface," and at 650, OTS may be sanitized, such as by wiping down a surface. At 655, test results may be received, such as through an interface, a printout, or through email, as non-limiting examples. At 660, OTS may be exited.

In some aspects, the user may activate an OTS by pressing a button on the interface. In some embodiments, the interface may have a motion sensor to sense when a user may be near to begin the process without pressing on the interface. Once an OTS is activated, a user may be prompted to answer questions. In some aspects, the questions may relate to the user's health, medical information, and general personal information, as non-limiting examples. In some implementations, the user may be required to answer additional questions based on the previous information provided to the interface. Once all information has been provided, the test may be activated by the user through the interface. The interface may prompt the user to place their eyes in front of the testing device for the test to begin. Once the users' eyes are in place they may be required to stay still while the test is being conducted.

In some aspects, the interface may notify the user when the test has been concluded, and the user may move away from the testing device. Once the test has concluded, the user may be prompted to clean the device. After the user has been instructed to clean the device, the user may clean the device as instructed. Once the device has been cleaned, the user may exit the testing position and receive their results from the interface. After the user is satisfied and receives their results. they may leave an OTS and the process has been completed.

Figure 7:
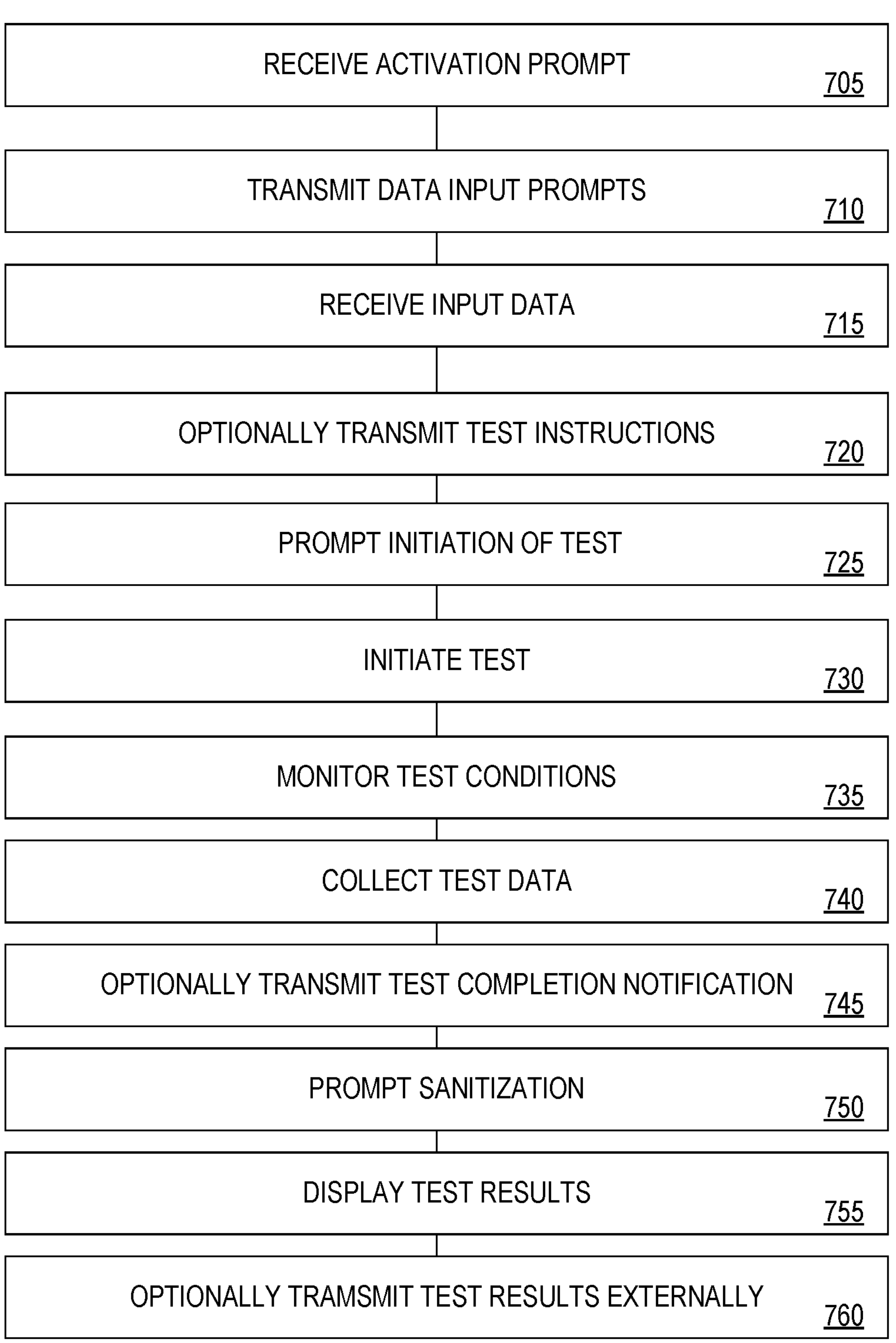
FIG. 7 illustrates exemplary method steps for screening for ophthalmic diseases, according to some embodiments of the present disclosure.

Referring now to FIG. 7, exemplary method steps for screening diseases are illustrated, according to some embodiments of the present disclosure. At 705, activation prompt may be received, such as when a user may enter an OTS. At 710, data input prompts may be transmitted, and at 715, input data may be received, such as name, age, or pre-existing conditions, as non-limiting examples. In some embodiments, test instructions may be transmitted, such as guidance to effectively acquire test data, information about the screening process, or how to disinfect the area, as non-limiting examples.

At 725, initiation of test may be prompted, and at 730, testing may initiate. As discussed above, this testing may proceed by capturing an image of the user's retina using the technologies described herein, such as an OCT apparatus or fundus camera. At 735, test conditions may be monitored, which may ensure that accurate testing data may be collected. If test conditions fall outside acceptable parameters, the testing process may be paused until or restarted when acceptable test conditions are detected. For example, if the imaging is inconclusive due to the presence of eyelashes, hair, or a blinking of the user, then the user may be prompted to attempt the test again. At 740, testing data may be collected. In some embodiments, this testing data may be analyzed on site at the OTS, while in other embodiments, communications devices within the OTS may cause the testing data to be transmitted remotely. In some implementations, at 745, test completion notification may be transmitted. At 750, sanitization may be prompted.

In some aspects, a sanitization prompt may prompt a user to manually sanitize an OTS. In some embodiments, sanitization prompt may trigger sanitization mechanisms within an OTS to sanitize. At 755, test results may be displayed. In some implementations, at 760, test results may be transmitted externally, such as to a third party or external database. Test results may be transmitted to a healthcare provider system, the user's email, or an OTS database, as non-limiting examples.

In some aspects, an OTS may activate before the process begins. After activation has been prompted an OTS may the ask the user for general information about themselves, and an OTS receives the information and processes it. Once processed, an OTS may prompt the user for any additional information regarding themselves based on their previous information provided. Once all the information is received by an OTS, the user may be prompted to start the test by an OTS, and an OTS may check lighting levels before the test may actually be initiated. In some implementations, the lighting may not be appropriate for the test, and the OTS may prompt the user to adjust the lighting before the test can begin.

In some embodiments, once the test starts, an OTS may record all test data and store it for when the test has concluded. Once the test concludes, an OTS may notify the user and prompt them to clean the testing device and surrounding areas. In some embodiments, an OTS may display instructions to the user on how to properly clean the device. Once an OTS has prompted the user to clean the testing device, it may deliver the results to the user once all data has been accurately collected. In some aspects, an OTS may deliver the test data to third party health facilities and doctors offices provided by the user.

Figure 8:
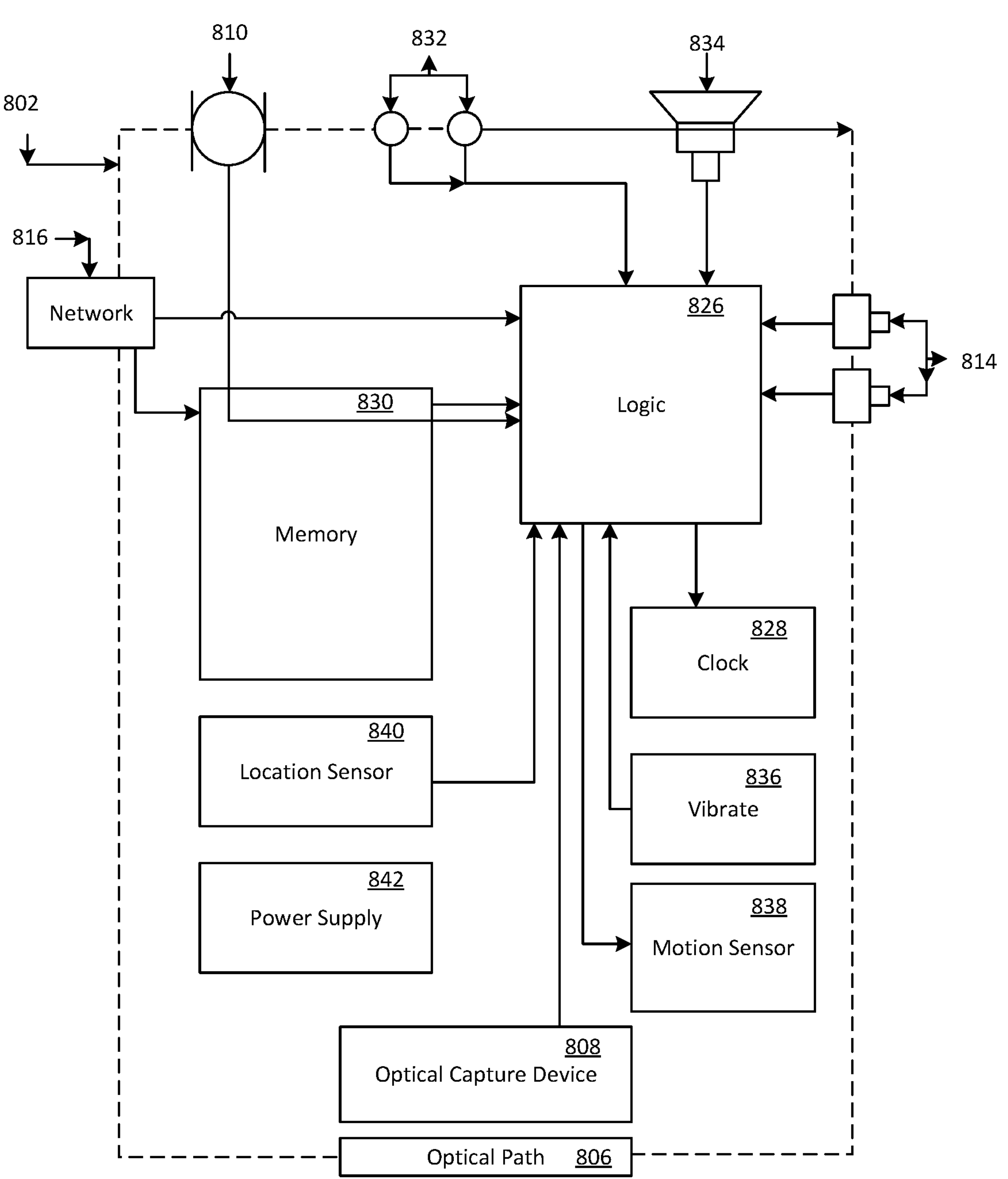
FIG. 8 illustrates a block diagram and components of an exemplary embodiment of an ophthalmic testing system, according to some embodiments of the present disclosure.

Referring now to FIG. 8, an exemplary block diagram and components of an exemplary embodiment of an OTS 802 is illustrated. The OTS 802 may comprise an optical capture device 808, which may capture an image and convert it to machine-compatible data, and an optical path 806, typically a lens, an aperture, or an image conduit to convey the image from the rendered document to the optical capture device 808. The optical capture device 808 may incorporate a Charge-Coupled Device (CCD), a Complementary Metal Oxide Semiconductor (CMOS) imaging device, or an optical sensor of another type.

In some embodiments, the OTS 802 may comprise a microphone 810, wherein the microphone 810 and associated circuitry may convert the sound of the environment, including spoken words, into machine-compatible signals. Input facilities 814 may exist in the form of buttons, scroll-wheels, or other tactile sensors such as touchpads. In some embodiments, input facilities 814 may include a touchscreen display. Visual feedback 832 to the user may occur through a visual display, touchscreen display, or indicator lights. Audible feedback 834 may be transmitted through a loudspeaker or other audio transducer. Tactile feedback may be provided through a vibration module 836.

In some aspects, the OTS 802 may comprise a motion sensor 838, wherein the motion sensor 838 and associated circuitry may convert the motion of the OTS 802 into machine-compatible signals. For example, the motion sensor 838 may comprise an accelerometer, which may be used to sense measurable physical acceleration, orientation, vibration, and other movements. In some embodiments, the motion sensor 838 may comprise a gyroscope or other device to sense different motions.

In some implementations, the OTS 802 may comprise a location sensor 840, wherein the location sensor 840 and associated circuitry may be used to determine the location of the device. The location sensor 840 may detect Global Position System (GPS) radio signals from satellites or may also use assisted GPS where the mobile device may use a cellular network to decrease the time necessary to determine location. In some embodiments, the location sensor 840 may use radio waves to determine the distance from known radio sources such as cellular towers to determine the location of the OTS 802. In some embodiments these radio signals may be used in addition to and/or in conjunction with GPS.

In some aspects, the mobile device 802 may comprise a logic module 826, which may place the components of the OTS 802 into electrical and logical communication. The electrical and logical communication may allow the components to interact. Accordingly, in some embodiments, the received signals from the components may be processed into different formats and/or interpretations to allow for the logical communication. The logic module 826 may be operable to read and write data and program instructions stored in associated storage 830, such as RAM, ROM, flash, or other suitable memory. In some aspects, the logic module 826 may read a time signal from the clock unit 828. In some embodiments, the OTS 802 may comprise an on-board power supply 832. In some embodiments, the OTS 802 may be powered from a tethered connection to another device, such as a Universal Serial Bus (USB) connection.

In some implementations, the OTS 802 may comprise a network interface 816, which may allow the OTS 802 to communicate and/or receive data to a network and/or an associated computing device. The network interface 816 may provide two-way data communication. For example, the network interface 816 may operate according to an internet protocol. As another example, the network interface 816 may comprise a local area network (LAN) card, which may allow a data communication connection to a compatible LAN. As another example, the network interface 816 may comprise a cellular antenna and associated circuitry, which may allow the mobile device to communicate over standard wireless data communication networks. In some implementations, the network interface 816 may comprise a Universal Serial Bus (USB) to supply power or transmit data. In some embodiments, other wireless links known to those skilled in the art may also be implemented.

Figure 9:
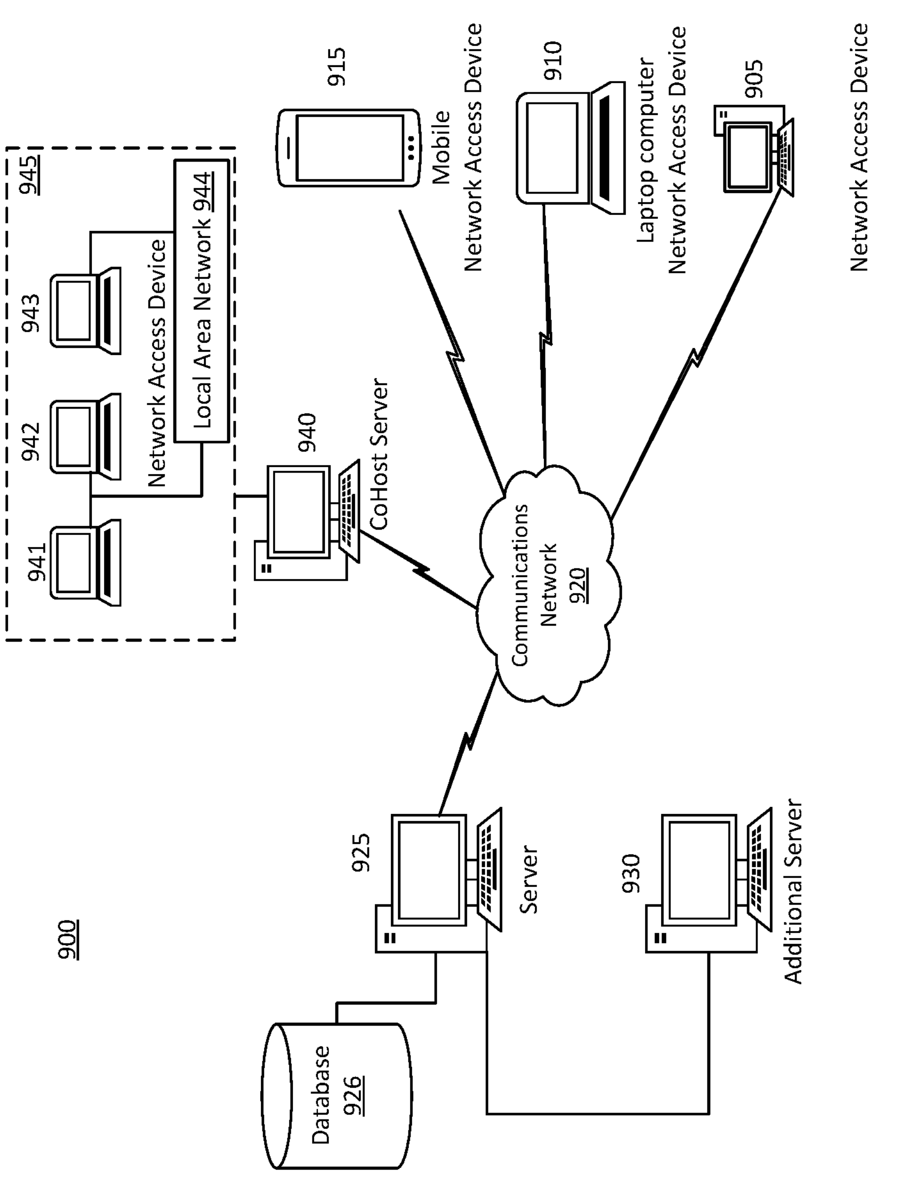
FIG. 9 illustrates an exemplary processing and interface system, according to some embodiments of the present disclosure.

Referring now to FIG. 9, an exemplary processing and interface system 900 is illustrated. In some aspects, access devices 915, 910, 905, such as a paired portable device 915 or laptop computer 910 may be able to communicate with an external server 925 though a communications network 920. The external server 925 may be in logical communication with a database 926, which may comprise data related to identification information and associated profile information. In some embodiments, the server 925 may be in logical communication with an additional server 930, which may comprise supplemental processing capabilities.

In some aspects, the server 925 and access devices 905, 910, 915 may be able to communicate with a cohost server 940 through a communications network 920. The cohost server 940 may be in logical communication with an internal network 945 comprising network access devices 941, 942, 943 and a local area network 944. For example, the cohost server 940 may comprise a payment service, such as PayPal or a social network, such as Facebook or a dating website, or an analysis server, such as a supercomputer.

Figure 10:
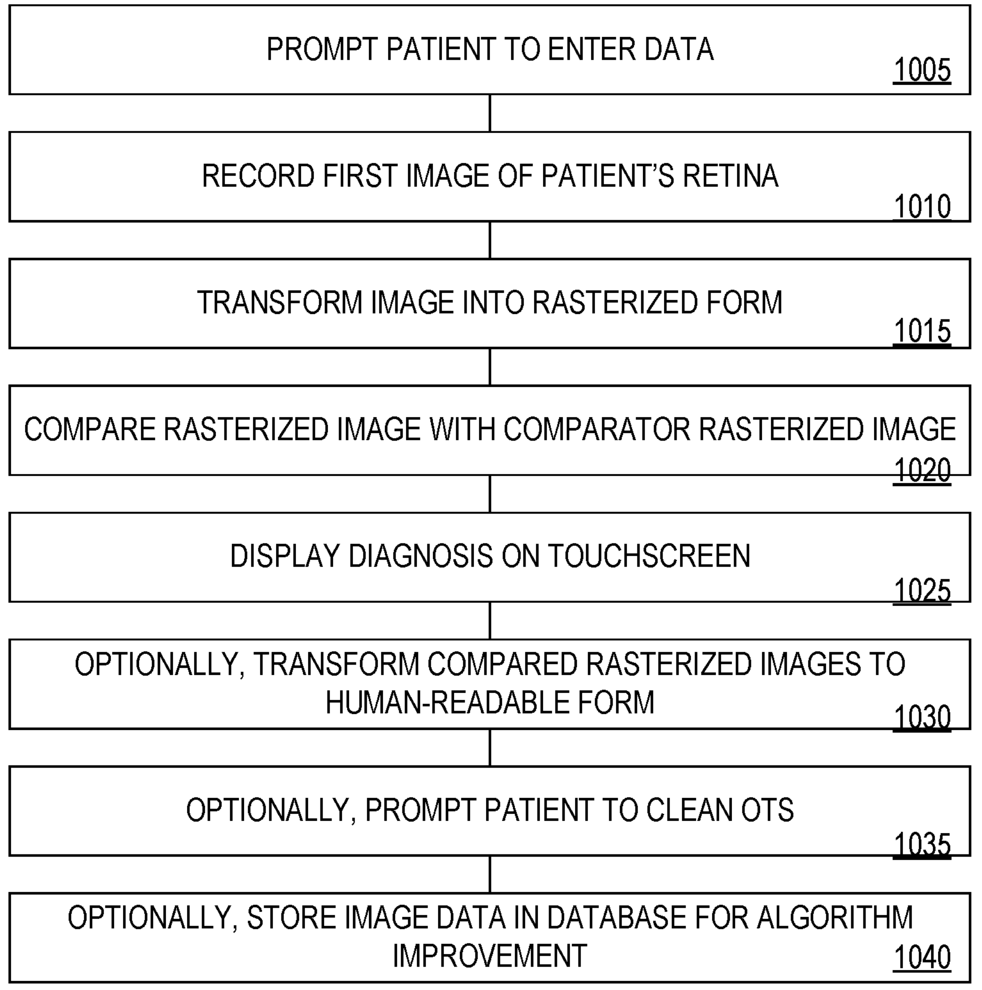
FIG. 10 illustrates exemplary method steps for screening for disease using an ophthalmic testing system, according to some embodiments of the present disclosure.

Referring now to FIG. 10, additional method steps for use in screening for diseases using an OTS are shown. At step 1005, a patient may be prompted to enter into a touchscreen health information about the patient. This health information may include, without limitation, information about the user's prior health history, height, weight, age, sex, or other information. Similarly, additional health or personal information may be determined via sensor in logical connection to the OTS. For example, the OTS may include a blood pressure cuff, pulse oximeter, pulse meter, or other apparatus for determining health information about the patient, as well as a global positioning system or other location-determination device to correlate a geographic location with the reading. At this stage, a desired diagnosis may also be input by the user (e.g., the user wishes to screen for cardiac concerns), although this is not necessary.

At step 1010, an imaging device may record a first image of at least one of the patient's retinas. This imaging device may include any of the devices described herein, such as an OCT apparatus or fundus camera. The resultant scan may then be stored in a memory in connection with the OST.

At step 1015, the scan may be transformed into a rasterized image. As discussed above, rasterization involves transforming an image into dots or pixels to expedite analysis. This transformation may occur at the OST or at a server remote from the OST. This server may obtain the image through a communication device in logical connection with the OST.

At step 1020, the rasterized scan may be compared to a rasterized image of a relevant retinal scan. For example, if the patient wishes to scan for cardiac disease (or for a co-indicator of cardiac disease, such as cataracts), then the rasterized scan may be compared with a rasterized image of a retinal scan of a "baseline" patient presenting with similar concerns. A pattern of pixels or dots associated with the relevant area of the eye may be compared to determine whether the patient's and the baseline patient's scans include similar patterns. In some embodiments, if the patient's scan and the baseline patient's scan exhibit similar patterns, these patterns may be compared with a rasterized scan of a patient who is not presenting with the identified concern to attempt to confirm whether the commonality is coincidental or indicative of an underlying disease. As above, this comparison may occur at the OST or at a remote server.

In some embodiments, the comparator baseline patient described above is a previous scan of the same patient's retina. For example, a diminishing thickness of a patient's retinal nerve fiber layer may be indicative of early-onset Alzheimer's disease. A patient wishing to be screened for Alzheimer's may wish to have their retinal scan compared with an earlier retinal scan to assess any change in the thickness of the retinal nerve fiber layer.

In some embodiments, the second rasterized image used for comparison may not correspond directly to an image of a retinal scan. Instead, the second rasterized image may comprise one or more known patterns of dots or pixels indicative of a retinal condition.

At step 1025, based upon the comparison of the rasterized images, the touchscreen may display one or more diagnoses. These diagnoses may include a primary diagnosis (e.g., the presence of cataracts) and a secondary diagnosis (e.g., the presence of cataracts is indicative of potential cardiac risk).

At optional step 1030, the rasterized images may be converted back to human-readable images, such as images in vector form. These images may be displayed on the touchscreen to provide a point of reference for the patient. In this way, for example, a comparison of the patient's retinal scan with the patient's previous retinal scan may be shown to illustrate a reduction in thickness of the retinal nerve fiber layer. In some embodiments, the retinal nerve fiber layer in each image may be highlighted or annotated to better educate the patient. This may include displaying diagnostic information (e.g., "The 1/1/2019 retinal scan shows a thicker retinal nerve fiber layer than the 1/1/2022 scan This may be indicative of Alzheimer's disease."

In exemplary embodiments, the primary diagnosis and the secondary diagnosis may be as follows, based upon the medical literature (as non-limiting examples):

| Basis of comparison | Primary diagnosis | Secondary diagnosis |
|---|---|---|
| Decrease in thickness of retinal nerve fiber layer | Decrease in thickness of retinal nerve fiber layer | Alzheimer's |
| Change in opacity of vitreous | Cataracts | Cardiac disease |
| Increase in Drusen observed | Macular degeneration | Alzheimer's, early death |
| Glaucoma progression based upon previous retinal scans | Early glaucoma | Blindness |

At optional step 1035, the patient may be prompted via the touchscreen to clean the ophthalmic testing device with a provided cleaner.

At optional step 1040, information about the scan may be stored in a database. This information may include the health or personal information obtained above (e.g., height, sex, GPS position). A preliminary diagnosis may be included with this scan. This preliminary diagnosis may also be a tag associated with the scan, to allow for easier retrieval of the scan based upon subsequent need (e.g., a query for a scan showing macular degeneration). In some embodiments, some personal information may be removed from the database entry (e.g., patient name). In this way, artificial intelligence or machine learning algorithms may be improved based upon the scan (or the rasterized form of the scan).

Conclusion

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. A method of diagnosing a disease risk using a self-administered ophthalmic testing system, the method comprising the steps of:

a. prompting a patient to enter into a touchscreen health information about the patient, wherein the touchscreen is in logical connection with a processor, a memory, and an imaging device;

b. recording, via the imaging device, a first image of at least one of the patient's retinas;

c. storing the first image in the memory;

d. transforming, via the processor, the first image into a first rasterized image;

e. creating a second rasterized image through machine learning processing;

f. comparing a component of the first rasterized image to a component of the second rasterized image; and g. based upon the comparison of the first and second rasterized images, causing the touchscreen to display a diagnosis of the disease risk.

2. The method of claim 1, wherein the imaging device comprises an optical coherence tomography apparatus.

3. The method of claim 2, wherein the disease risk is early-onset Alzheimer's disease.

4. The method of claim 3, wherein the component of the first rasterized image and the component of the second rasterized image is a thickness of the patient's retinal nerve fiber layer, and wherein the touchscreen displays a positive diagnosis of a risk of early-onset Alzheimer's disease based upon a decrease in thickness of the patient's retinal nerve fiber layer.

5. The method of claim 4, wherein the second rasterized image is a prerecorded image of a retina of a person having a cataract as processed by a machine learning algorithm.

6. The method of claim 5, wherein the disease risk is a risk of cardiac disease.

7. The method of claim 6, wherein the component of the first rasterized image is a quality of a vitreous of the patient's eye, the component of the second rasterized image is a quality of a vitreous of the retina of the person having a cataract, and wherein the touchscreen displays a positive diagnosis of a risk of cardiac disease based upon a comparison of the quality of the components of the first and second rasterized images.

8. The method of claim 2, wherein the disease risk is early death, and wherein the component of the first rasterized image and the component of the second rasterized image is a macula of the patient's retina, and wherein the touchscreen displays a positive diagnosis of a risk of early death based upon a degeneration in the macula.

9. The method of claim 1, further comprising the steps of:

h. converting the first rasterized image and the second rasterized image to a first vector image and a second vector image, respectively;

i. highlighting the component of the first rasterized image and the component of the second rasterized image as the components appear in the first and second vector images, respectively;

j. causing the touchscreen to display the first and second vector images; and k. displaying diagnostic information relating to the comparison of the components.

10. The method of claim 1, wherein the imaging device comprises a fundus camera.

11. The method of claim 1, wherein the imaging device comprises a slit lamp microscope.

12. The method of claim 1, wherein the self-administered ophthalmic testing device is in logical communication with a communications device, and wherein the method further comprises the steps of:

h. transmitting the first image via the communications device to a remote server; and i. receiving via the communications device a result of a comparison between the first image and the second image.

13. The method of claim 12, further comprising the step of storing the first image and the health information on the remote server.

14. The method of claim 13, wherein the ophthalmic testing device further comprises a global positioning system, and wherein the method further comprises the step of associating the first image with a first global positioning system reading.

15. The method of claim 12, further comprising the steps of:

j. converting the first rasterized image and the second rasterized image to a first vector image and a second vector image, respectively;

k. highlighting the component of the first rasterized image and the component of the second rasterized image as the components appear in the first and second vector images, respectively;

l. causing the touchscreen to display the first and second vector images; and m. displaying diagnostic information relating to the comparison of the components, wherein the diagnostic information includes information about other patients having a second global positioning system reading within a predefined threshold of the first reading.

16. The method of claim 15, wherein the health information comprises one or more of: age, sex, or weight, and wherein the diagnostic information includes information about other patients having comparable health information.

17. The method of claim 1, wherein the comparison between the first rasterized image and the second rasterized image is based upon a comparison of patterns of pixels in the first rasterized image and the second rasterized image.

* * * * *